United States Patent [19]

Hori

[11] Patent Number: 5,347,988
[45] Date of Patent: Sep. 20, 1994

[54] ENDOSCOPE COUPLER WITH LIQUID INTERFACE

[75] Inventor: Koichiro Hori, Framingham, Mass.

[73] Assignee: Linvatec Corporation, Largo, Fla.

[21] Appl. No.: 882,395

[22] Filed: May 13, 1992

[51] Int. Cl.$^5$ .................................................. A61B 1/00
[52] U.S. Cl. ............................................. 126/4; 354/62
[58] Field of Search .......................... 128/4, 6; 354/62; 403/37; 358/98

[56] References Cited

U.S. PATENT DOCUMENTS

| | | | |
|---|---|---|---|
| 4,076,018 | 2/1978 | Heckele | 128/6 |
| 4,569,333 | 2/1986 | Bel et al. | 128/4 |
| 4,611,888 | 9/1986 | Prenovitz et al. | 350/96.22 |
| 4,641,912 | 2/1987 | Goldenberg | 350/96.10 |
| 4,722,000 | 1/1988 | Chatenever | 358/98 |
| 4,740,058 | 4/1988 | Hori et al. | 350/255 |
| 4,742,818 | 5/1988 | Hughes et al. | 126/6 |
| 4,781,448 | 11/1988 | Chatenever et al. | 350/429 |
| 4,805,598 | 2/1989 | Ueda | 128/6 |
| 4,807,594 | 2/1989 | Chatenever | 128/4 |
| 4,844,071 | 7/1989 | Chen et al. | 128/6 |
| 4,851,866 | 7/1989 | Ciarlei et al. | 354/62 |
| 4,863,304 | 9/1989 | Bauer et al. | 403/37 |
| 4,969,450 | 11/1990 | Chinnock et al. | 128/6 |
| 5,125,394 | 6/1992 | Chatenever et al. | 128/4 |

*Primary Examiner*—Richard J. Apley
*Assistant Examiner*—Beverly A. Meindl

[57] ABSTRACT

An improved endoscope assembly includes a quantity of optically transparent liquid filling the space between facing windows of adjoining mechanically and optically coupled components to eliminate fogging due to condensation and thereby provide improved image quality. One component includes a male connector with its window at its mating end. The other component has a recess defined therein for receiving the male connector. A stop member on the connector abuts the other component to define maximal insertion of the connector and establish a space between the windows for retaining the liquid. The space between the windows is sufficiently small to permit retention of the liquid in the recess by means of surface tension.

20 Claims, 1 Drawing Sheet

U.S. Patent   Sep. 20, 1994   5,347,988
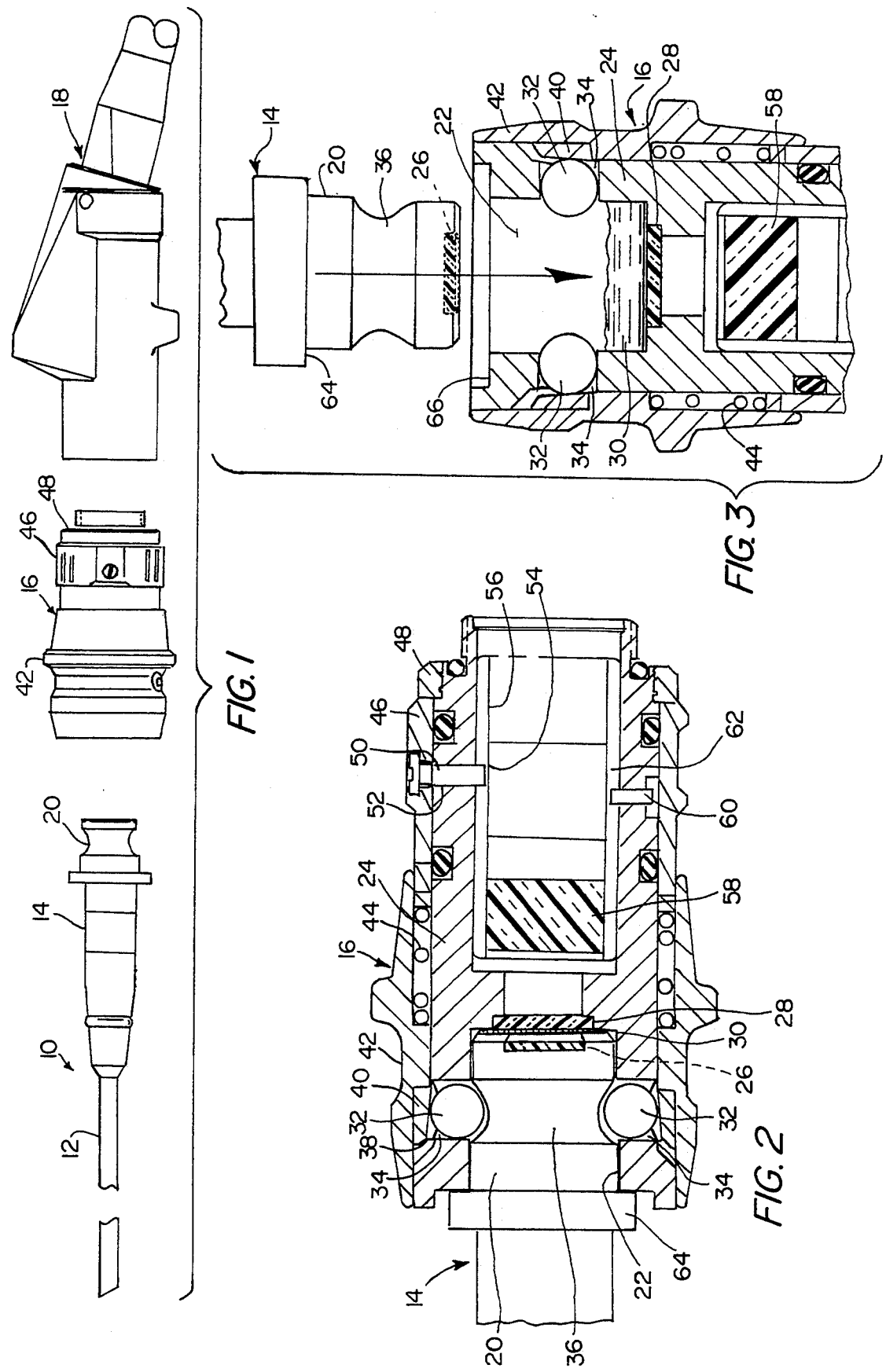

ENDOSCOPE COUPLER WITH LIQUID INTERFACE

BACKGROUND OF THE INVENTION

1. Technical Field

The present invention pertains to a method and apparatus for mechanically and optically coupling an endoscope to a video camera, or the like. In particular, the invention is directed to eliminating fogging of adjacent optical windows in two mechanically and optically coupled devices.

2. Discussion of the Prior Art

Endoscopes have been successfully utilized in surgery for viewing body cavities and organs to permit diagnoses and surgical procedures to be performed internally without requiring open surgery or other invasive procedures. An endoscope is typically inserted through a small incision portal providing access to a body cavity. A lens at a distal end of the endoscope is positioned to receive light reflected from a site to be observed, and images of that site can be viewed remotely in conducting histological examinations and performing closed, or endoscopic, surgery. As utilized herein, the term endoscope refers generically to viewing devices for remotely observing otherwise inaccessible body cavities with minimal trauma and intrusion, and includes, but is not limited to, arthroscopes, colonoscopes, bronchoscopes, hysteroscopes, cystoscopes, sigmoidoscopes, laparoscopes and ureterscopes.

Endoscopes are sometimes supplied with an eyepiece at a proximal end thereof, and relay lenses in the endoscope typically produce an image for direct viewing through the eyepiece. However, adaption of video camera technology to endoscopy imaging has enabled the output image of an endoscope to be viewed on a video monitor via a video camera electronically connected with the video monitor and optically and mechanically coupled to the proximal end of the endoscope. Indirect or video monitor viewing of endoscopic images provides numerous benefits over direct viewing through an eyepiece, including: protection of viewer's vision when high intensity illumination passing through the endoscope reflects off bodily tissue at the site to be viewed; enhancement of an operator's comfort and freedom of movement; increased utility and efficiency of endoscopes; reduction in the time required to conduct endoscopic procedures; simultaneous viewing of endoscopic images by more than one person; and recordation and real time transmission of surgical procedures. When a video camera is utilized with an endoscope, an endoscope coupler is required to mechanically and optically couple the proximal end of the endoscope with the video camera, illustrative endoscope couplers being shown in U.S. Pat. Nos.: 4,569,333 (Bel et al); 4,611,888 (Prenovitz et al); 4,722,000 (Chatenever); 4,740,058 (Hori et al); 4,781,448 (Chatenever et al); 4,807,594 (Chatenever); 4,844,071 (Chen et al); 4,851,866 (Ciarlei et al); 4,863,304 (Bauer et al); and 4,969,450 (Chinnock et al).

One recurring problem in endoscope coupler design is poor image quality resulting from moisture, condensation or residue from dried moisture on transparent windows optically coupling various components of the assembly. More particularly, it is conventional for a complete endoscope assembly to include an extended probe referred to as the endoscope, an endoscope coupler and an image-forming device such as a video camera or optical eyepiece. The optical path through each of these elements is typically terminated by a window, flat or optically powered, and it is a recognized problem that moisture, condensation or residue tends to form on these windows resulting in the degradation of the surgeon's view of the surgical site. For example, the endoscope and coupler are typically sterilized by immersion in bactericidal solutions such as Cidex or Sporiciden and then rinsed with distilled water, usually leaving some residual moisture on the optical windows. If steps are taken to dry the windows, a residue may still remain. Further, moisture from surrounding air and surgical irrigation may condense on the window surfaces. In any case, the moisture or residue interferes with the surgeon's view of the surgical site.

There are numerous patents directed to methods and apparatus for eliminating "fogging" in an endoscope assembly. For example in the Chatenever '000 patent and in U.S. Pat. No. 4,076,018 (Heckele), fogging due to condensation is eliminated by providing resistive heating elements at various locations in the assembly. The presence of the resistive heating elements adds undesired complexity and cost. The Chatenever '594 patent discloses prevention of condensation by providing glass-to-glass contact between the proximal endoscope window and the adjacent distal window of the coupler. Such glass-to-glass contact requires relatively precise mechanical tolerances on the manufactured components and their assembly. The Bauer '304 patent discloses an attempt to eliminate condensation by flowing air through appropriate spaces in the endoscope assembly, thereby unduly complicating the overall design and increasing the cost. Similarly, in the Ciarlei et al '866 patent, a vent is disclosed for connection to a suction adapter employed to withdraw moisture, again complicating the structure of the system and requiring the surgeon to couple a source of suction to the vent whenever fogging is detected. It is also common in various endoscopic procedures to provide ample flow of irrigating liquid to flush debris from the surgical site. The application of suction to the instrument, as suggested by Ciarlei et al, would tend to cause the assembly to be filled with the irrigating liquid. The approach disclosed in the Prenovitz et al '888 patent is to provide O-rings at the interfaces between all components of the coupler, between the coupler and the endoscope, and between the coupler and the camera. The resulting structure is relatively complex and difficult to implement.

Each of the above-described patents is directed to a technique for avoiding fogging due to condensation. None of these patents addresses the issue of preventing degradation of image quality due to residue of dried moisture on the optical windows. U.S. Pat. No. 4,805,598 (Ueda), on the other hand, suggests that a viscous gel-like substance, free from moisture, can be utilized to fill the space between adjacent associated lenses of endoscope system components to prevent condensation of water on the lenses. The gel may be provided at one or more locations in the optical system but it appears that the gel is applied only during manufacture; that is, the gel is not applied during assembly of the components in the surgical operating theater. Accordingly, it is quite likely that condensation will form on the windows of adjacent components of the optical assembly.

Other patents having general relevance to the present invention, although not directly addressing the problem of fogging, are U.S. Pat. No. 4,641,912 (Goldenberg) disclosing the use of a water mass for coupling laser energy into an optical fiber waveguide of an endoscope, and U.S. Pat. No. 4,742,818 (Hughes et al) disclosing a seal located between components of the focusing mechanism of an endoscope to prevent sterilizing liquid from leaking between them during sterilization.

Until the present invention there has been no effective technique for eliminating both condensation on optical windows and moisture and/or residue of such moisture in an endoscope assembly.

SUMMARY OF THE INVENTION

Accordingly, it is an object of the invention to provide a method and apparatus for avoiding condensation, moisture and moisture residue on optical windows of an endoscope assembly without incorporating the above-mentioned disadvantages.

It is a further object of the present invention to provide an endoscope system, and a method for its assembly in a surgical operating theater, whereby condensation or fogging on optical windows of the assembly is eliminated without unduly complicating the assembly steps performed by operating theater personnel or complicating the structure of the overall assembly.

According to the invention an endoscope system comprises an endoscope having a male connector and an endoscope coupler connecting the endoscope to a video camera or other image forming device. The coupler includes a recess for receiving the male connector in a relatively snug fit. A window at the end of the connector is axially spaced a short distance from a window in the coupler recess in the assembled system. Prior to insertion of the connector, a small quantity of optically transparent liquid, typically distilled water, is placed in the recess. Upon insertion of the connector excess water is extruded out around the connector from the recess, thereby eliminating air from the space between the two windows and preventing any possibility of fogging while simultaneously preventing drops of moisture or residue of dried moisture from interfering with the formation of a clear image. In the preferred embodiment the dimensions of the male connector and the recess are sufficiently small as to permit surface tension to prevent water from subsequently leaking out of the recess, thereby eliminating the need for seals or the like to maintain the liquid between the windows.

Other objects and advantages of the present invention will become apparent from the following description of the preferred embodiment taken in conjunction with the accompanying drawings wherein like parts each of the several figures are identified by the same reference characters.

BRIEF DESCRIPTION OF THE DRAWINGS

FIG. 1 is an exploded side view of an endoscope assembly, including an endoscope, a coupler and a camera, employing the principles of the present invention;

FIG. 2 is a side view in longitudinal section of a connector of the endoscope of FIG. 1 received in a recess defined in the coupler of FIG. 1; and FIG. 3 is a partially diagrammatic side view in longitudinal section illustrating the insertion of the connector of FIG. 2 into a liquid-containing recess in the coupler in accordance with the principles of the present invention.

DESCRIPTION OF THE PREFERRED EMBODIMENTS

Referring to the drawings in greater detail, an endoscope assembly according to the present invention is illustrated in FIG. 1 and includes an endoscope 10 having a conventional elongated optical probe 12. Probe 12 may be flexible or not and, if flexible, typically includes a first optical fiber or fiber bundle for transmitting light to the interior of a patient's body cavity and a second optical fiber or fiber bundle for conducting reflected light from the body cavity to an imaging device. If probe 12 is rigid it typically includes a fixed optical system. Where desired, the elongated probe 12 may be inserted into a tubular bore defined in a larger diameter elongated member having one or more further bores defined therein for surgical instrument and fluid conduits. Endoscope 10 also includes a terminal member 14 permanently affixed to the proximal end of optical probe 12. Terminal member 14 optically and mechanically couples the elongated optical probe 12 to an endoscope coupler 16 serving to mechanically and optically couple terminal member 14 to a conventional video camera or other imaging device indicated generally at 18. A proximally extending male connector 20 is defined as part of terminal member 14 and is adapted to be received in a recess 22 defined in the distal end of a hollow and generally cylindrical body 24 of coupler 16 (FIGS. 2 and 3). Male connector 20 and recess 22 are generally cylindrical in cross-section.

A window 26 is centrally disposed at the proximal end of connector 20 and faces a similar window 28 centrally disposed in the distally facing end of recess 22 in body 24. Light traversing the optical paths through endoscope 10 and coupler 12 must pass through these windows which may be flat or contoured to serve as lenses. In accordance with the present invention a quantity 30 of transparent liquid, typically distilled water, is disposed between windows 26 and 28 to completely fill the space therebetween and prevent any condensation or residue from forming on the windows. Accordingly, windows 26, 28 are disposed in respective annular recesses in connector 20 and the base of recess 22, and are sealed in place by suitable adhesive or the like to prevent leakage of the liquid into the interiors of connector 20 and coupler 16.

Terminal member 14 of endoscope 10 is releasably connected to coupler 16 in a generally conventional manner. In particular, a plurality of locking balls 32 are carried in respective radial bores 34 in the main body 24 of the coupler, and engage an annular groove 36 formed about male connector 20. Groove 36 has an arcuate cross-section with a radius of curvature slightly larger than the radius of balls 32. The locking balls 32 are held in groove 36 by an interiorly facing cylindrical surface 38 of an annular plastic insert 40. The insert has its outer surface secured to and movable with a locking sleeve 42 retained coaxially about the coupler body 24 for axial movement relative to that body. Locking sleeve 42 is biased by a helical spring 44, also disposed about body 24, toward the distal end of the coupler (i.e., the end receiving male connector 20 of the endoscope). In order to remove male connector 20 from recess 22, locking sleeve 42 is moved axially along the coupler body 24 (i.e., rightwardly in FIG. 2), displacing insert 40 axially and thereby allowing the locking balls 32 to be moved radially outward in bores 34 so as to be removed from the annular groove 36 of connector 20. This movement of the locking balls is achieved by withdrawing connector 20 from recess 22, thereby causing the moving arcuate surface of groove 36 to force the balls radially outward into bores 34 with a camming action and permitting complete withdrawal of connector 20. Locking sleeve 42 is similarly moved rightwardly when it is desired to insert connector 20 into recess 22. In such a case, a chamfered annular edge of the connector initially forces the locking balls radially outward into bores 34, the balls being maintained in their outward position by the cylindrical end section of the connector. Upon radial alignment between the groove 36 and bores 34 (i.e., the maximal insertion of the connector into the recess), the locking balls are free to move inwardly and can be so urged by returning locking sleeve and its attached insert 40 to their quiescent positions (i.e, to the left in FIG. 2) under the bias of spring 44.

Spring 44 is urged against locking sleeve 42 by a focus ring 46 disposed about coupler body 24 and retained thereon by a threaded sleeve 48. A focusing pin 50, secured to focus ring 46, extends radially through a circumferential slot 52 defined in body 24 and into a helical slot 54 defined in an inner lens carrier 56 supporting a focusing lens 58. A dowel pin 60, secured to and extending radially from body 24, is received in an axially extending slot 62 defined in lens carrier 56. Dowel pin 60 serves to permit lens carrier 56 to move axially within body 24 while preventing the lens carrier from rotating. Accordingly, when the focus ring 46 is rotated, focusing pin 50 exerts an axial force on the walls of the helical slot 54, causing lens carrier 56 and focusing lens 58 to move axially to adjust the endoscope system focus.

Prior to assembling the components, a quantity 30 of optically transparent liquid, typically distilled water, is disposed in recess 20 as shown in FIG. 3. The quantity of water may be equal to or less than the capacity of the recess. When the male connector 20 is inserted into the recess, any water exceeding the volume of the space between connector 20 and recess 22 is extruded out through the annular gap between these components. Accordingly, no air can remain present in the space between the windows 26 and 28 when the assembly is complete, as shown in FIG. 2, and no condensation droplets of moisture or residue on either window can interfere with accurate formation of the image.

The fit of connector 20 in recess 22 is required to provide some axial space between windows 26 and 28 after the assembly is completed. This axial space is typically in the range of a few thousandths of an inch to several tens of thousandths of an inch, and preferably on the order of 0.010 inch. Connector 20 is provided with an annular stop flange extending radially outward at a location permitting it to abut an annular shoulder 66 surrounding the distal end of the recess 22, thereby preventing windows 26, 28 from contacting one another. Alternatively, spacer members may be provided in recess 22 to contact connector 20 and assure that windows 26, 28 remain properly spaced from one another. Although connector 20 has been illustrated and described as being formed on terminal member 14 while recess 22 is formed in coupler 16, the opposite arrangement is also possible within the scope of the present invention.

The cross-sectional shapes of connector 20 and recess 22 are desirably sufficiently closely matched to assure that water is retained in the recess by surface tension while allowing ready removal and insertion of the male connector. A circumferential clearance or gap on the order of 0.002 inch is appropriate for this purpose. In order to assure smooth insertion of connector 20 into recess 22, terminal member 14, including connector 20, may be molded of a plastic material such as that sold under the trademark "Delrin", while coupler body 24 may be made of aluminum, or the like.

It will be appreciated that the present invention provides an extremely simple yet highly reliable method and apparatus for eliminating condensation between the optical components of an endoscope assembly. The surgeon needs simply to pour a small quantity of distilled water into recess 22 before connecting the endoscope to the coupler. The quantity of water must at least equal the volume of the space remaining between windows 26, 28 after connection of the components, thereby preventing any condensation from forming on the windows. Accordingly, residue from drying moisture is also eliminated. Preferably, the optical characteristics of the endoscope assembly are such that light rays passing through the water in the axial gap between windows 26, 28 are collimated, thereby simplifying the overall optical design of the assembly and rendering the spacing of the windows less critical than would otherwise be the case. By comparison, it is not possible to design a conventional endoscope to compensate for the presence of uncertain amounts of disinfecting or rinsing fluids.

Assembly of the components in practicing the present invention can readily be accomplished utilizing design and manufacturing techniques well understood by those of ordinary skill in the art. The dimensional requirements for the system components are much less critical than in the assembly disclosed in the Chatenever '594 patent, for example, which requires glass-to-glass contact between the windows of adjacent components of an endoscope assembly in order to eliminate condensation. The principles of the invention can be employed in joining other components of the endoscope system, if needed, or components of other optical instruments.

According to the invention, the problem of condensation addressed extensively in the prior art is eliminated in a simple and essentially cost-free fashion, thereby eliminating image impairment due to residue from dried moisture or from varying amounts of liquid on the windows.

Having described the preferred and alternative embodiments of a new and improved endoscope system, it is believed that other modifications, variations and changes will be suggested to persons skilled in the art in view of the teachings set forth herein. It is therefore to be understood that all such variations, modifications and changes are believed to fall within the scope of the present invention as defined by the appended claims.

What is claimed is:

1. An endoscope assembly, consisting essentially of:
   an elongated endoscope having a distal end and a proximal end with a first transparent window disposed in said proximal end;
   a coupler having a distal end with a second transparent window disposed therein, and a proximal end adapted for connection to apparatus for forming a visible image; and
   joining means for connecting said endoscope to said coupler with a predetermined space between said first and second windows, the size of said space being selected to permit substantially unimpeded transmission of light therethrough when the space is filled with a transparent liquid.

2. An endoscope assembly as recited in claim 1 wherein said joining means includes a recess of predetermined depth formed in said distal end of said coupler, said second window being secured in fluid sealing relation at an innermost part of said recess, and a male connector formed on said proximal end of said endoscope and adapted for insertion into said recess, wherein said first window is secured in fluid sealing relation to said connector, and means for limiting the depth of insertion of said connector into said recess to establish said predetermined space between said first and second windows.

3. The endoscope assembly as recited in claim 2 wherein said means for limiting comprises stop means disposed on said connector for abutting a surface on said coupler.

4. The endoscope assembly as recited in claim 2 wherein said male connector and said recess have similar cross-sectional shapes and are closely sized with respect to one another such that said liquid is retained in said recess by surface tension.

5. An endoscope for use with an optical coupler, said coupler having a forward end and a transparent coupler window at the base of a recess formed in said forward end, and a rearward end adapted to be mechanically and optically coupled to a camera, said endoscope consisting essentially of:
  an elongated probe having a distal end and a proximal end, said probe including a transparent endoscope window disposed at said proximal end, and means for positioning said endoscope window within the recess in the coupler in spaced relation to the coupler window; and
  means for cooperating with the recess in the coupler to retain a quantity of transparent liquid between said endoscope window and the coupler window.

6. The endoscope as recited in claim 5 wherein said means for cooperating comprises an elongated male connector formed on said proximal end of said endoscope for fitting closely within the recess in the coupler to retain said fluid in the recess by means of surface tension.

7. The endoscope as recited in claim 6 wherein said transparent endoscope window is mounted on a proximal end of said male connector.

8. The endoscope as recited in claim 7 further comprising stop means disposed on said male connector for abutting a surface of the coupler in order to limit insertion of said male connector into the recess and thereby control the spacing of said windows.

9. In an assembly comprising an endoscope and a coupler for optically coupling the endoscope to an image forming optical device, wherein the endoscope includes an elongated optical probe and a connector disposed at a proximal end of the probe, wherein one of the coupler and connector defines a recess for axially receiving a male member comprised by the other of the coupler and connector, and wherein a first optical window is disposed at an interior end of the recess and a second optical window is disposed at the received end of the male member, the improvement comprising essentially of:
  cooperating spacing means on the male member and coupler defining a predetermined axial space between the optical windows when said male member is maximally inserted into said recess; and
  means for confining a quantity of optically transparent liquid in said recess to fill said predetermined axial space between the optical windows.

10. The improvement as recited in claim 9 wherein said cooperative spacing means comprises an abutment surface as part of said one of the coupler and connector, and flange means on the male member for abutting said abutment surface, the axial length of the recess from said abutment surface to said interior end being greater than the length of the male member as measured from said flange means to the received end of the male member.

11. The improvement of claim 10 wherein said flange means surrounds said male member, and wherein said abutment surface is an annular shoulder.

12. The improvement as recited in claim 9 wherein the recess is formed in said coupler and the male member is comprised by the connector.

13. The improvement as recited in claim 9 wherein the male member and recess are correspondingly shaped and sized with respect to one another such that said quantity of liquid is retained between the optical windows by surface tension.

14. The improvement as recited in claim 13 wherein the male member and recess are cylindrical, the recess being sufficiently greater in diameter than the male member to permit ready insertion and withdrawal of the male member into and out of the recess, and to allow extrusion of any excess liquid from the recess between the windows upon insertion of the male member into the recess while assuring that the liquid is retained in the recess by surface tension.

15. The improvement as recited in claim 9 wherein the connector and coupler further comprise cooperating retainer means for releasably retaining the male member within the recess.

16. In combination:
  an endoscope consisting essentially of a male connector and an elongated optical probe, said male connector having a first window at an exposed end thereof;
  a coupler having a distal end with a recess defined therein for receiving said connector, said recess having a second window at its base;
  means for maintaining a predetermined spacing between said windows when said connector is maximally inserted into said recess; and
  a quantity of optically transparent liquid disposed between said windows and filling said predetermined spacing.

17. The combination as recited in claim 16 further comprising stop means disposed on said male connector for abutting said distal end of said coupler when said connector is maximally inserted in said recess, the depth of the recess being greater than the length of said connector in said recess, whereby said first and second windows are spaced from one another when said stop means abuts said distal end of said coupler.

18. The combination as recited in claim 16 wherein said connector and recess have corresponding cross-sectional shapes and are sized with respect to one another such that said liquid is retained in said recess by surface tension.

19. A method for assembling an optical instrument consisting essentially of first and second components of the first component including an extended male connector having a first optical window at its end, the second component having a body defining a recess for receiving the male connector, the recess having a second optical window at its base, the first and second components including cooperative spacing means defining a space having a predetermined volume between the windows when the male connector is maximally inserted into the recess, said method comprising the steps of:

disposing a volume of optically transparent liquid in the recess, said volume of liquid being greater than the predetermined volume of the space between the windows;

inserting the male connector into the recess to extrude all liquid in excess of the predetermined volume from said recess such that the recess remains filled with said liquid; and releasably joining the first and second components.

20. The method of claim 19 wherein said liquid is retained in said recess by surface tension.

* * * * *